(12) United States Patent
Ali et al.

(10) Patent No.: US 9,320,638 B2
(45) Date of Patent: Apr. 26, 2016

(54) FIXATOR

(75) Inventors: Bajwa Ali, North Yorkshire (GB); Linda Pomeroy, Isle of Dogs (GB)

(73) Assignee: Cambfix Limited (GB)

( * ) Notice: Subject to any disclaimer, the term of this patent is extended or adjusted under 35 U.S.C. 154(b) by 1245 days.

(21) Appl. No.: 13/202,180

(22) PCT Filed: Feb. 19, 2010

(86) PCT No.: PCT/GB2010/050289
§ 371 (c)(1),
(2), (4) Date: Aug. 18, 2011

(87) PCT Pub. No.: WO2010/094971
PCT Pub. Date: Aug. 26, 2010

(65) Prior Publication Data
US 2011/0301610 A1    Dec. 8, 2011

(30) Foreign Application Priority Data

Feb. 20, 2009 (GB) .................................. 0902881.2

(51) Int. Cl.
*A61F 13/00* (2006.01)
*A61B 19/00* (2006.01)
(Continued)

(52) U.S. Cl.
CPC ............. *A61F 5/05866* (2013.01); *A61B 17/00* (2013.01); *A61B 17/17* (2013.01);
(Continued)

(58) Field of Classification Search
CPC ...... A61B 17/00; A61B 17/17; A61B 17/171; A61B 17/1739; A61B 17/1764; A61F 5/00; A61F 5/01; A61F 5/0102; A61F 5/0125; A61F 5/013; A61F 5/0132; A61F 5/0134; A61F 5/0137; A61F 5/04; A61F 5/042; A61F 5/048; A61F 5/058

USPC ................. 128/846, 869, 877–879, 881–882; 602/5, 12, 16, 20–21, 23–27, 32; 606/53, 54, 57, 60, 278, 86 R, 88, 90
See application file for complete search history.

(56) References Cited

U.S. PATENT DOCUMENTS 1,384,257 A * 7/1921 Hilgers ........................... 602/25
1,789,060 A    1/1931 Weisenbach
(Continued)

FOREIGN PATENT DOCUMENTS

DE        82 161 C      7/1895
EP        1382317 A     1/2004
(Continued)

OTHER PUBLICATIONS

Search Report for corresponding GB 0902881.2, Completed May 4, 2009 by Miss M. Rasmussen.
(Continued)

*Primary Examiner* — Alireza Nia
*Assistant Examiner* — Brandon L Jackson
(74) *Attorney, Agent, or Firm* — Tarolli, Sundheim, Covell & Tummino LLP

(57) ABSTRACT

We describe fixator (10) comprising an articulated bracelet (12). The bracele comprises a plurality of elements (24,26) arranged in a plurality of rows. The elements have complementary linking means (48,62) to permit linking the rows of elements together in an articulated or fixed relationship. One or more of the plurality of elements comprises means (34) for receiving and engaging at least a portion of a connecting device (16) such that the position of the connecting device can be altered around the bracelet or the limb that it is mounted on. The fixator further comprises an articulated connecting device, a rod and a hinge device.

19 Claims, 12 Drawing Sheets

(51) Int. Cl.
| | |
|---|---|
| *A61F 5/37* | (2006.01) |
| *A61F 5/00* | (2006.01) |
| *A61F 5/04* | (2006.01) |
| *A61B 17/56* | (2006.01) |
| *A61B 17/00* | (2006.01) |
| *A61F 4/00* | (2006.01) |
| *A61B 17/68* | (2006.01) |
| *A61F 2/30* | (2006.01) |
| *A61F 2/46* | (2006.01) |
| *A61F 2/00* | (2006.01) |
| *A61B 17/70* | (2006.01) |
| *A61F 5/058* | (2006.01) |
| *A61F 5/01* | (2006.01) |
| *A61B 17/17* | (2006.01) |
| *A61F 5/048* | (2006.01) |
| *A61F 5/042* | (2006.01) |

(52) U.S. Cl.
CPC .......... *A61B 17/171* (2013.01); *A61B 17/1739* (2013.01); *A61B 17/1764* (2013.01); *A61F 5/00* (2013.01); *A61F 5/01* (2013.01); *A61F 5/0102* (2013.01); *A61F 5/0125* (2013.01); *A61F 5/04* (2013.01); *A61F 5/042* (2013.01); *A61F 5/048* (2013.01); *A61F 5/058* (2013.01)

(56) References Cited

U.S. PATENT DOCUMENTS

| | | | | |
|---|---|---|---|---|
| 2,055,024 | A * | 9/1936 | Bittner, Jr. | 606/56 |
| 3,651,803 | A * | 3/1972 | Bimler | 602/16 |
| 4,180,870 | A | 1/1980 | Radulovic et al. | |
| 4,336,796 | A * | 6/1982 | Andrews et al. | 602/23 |
| 4,497,315 | A | 2/1985 | Fettweis et al. | |
| 4,538,600 | A * | 9/1985 | Hepburn | 602/16 |
| 4,677,971 | A | 7/1987 | Lindermann | |
| 4,834,057 | A | 5/1989 | McLeod, Jr. | |
| 4,941,460 | A | 7/1990 | Working | |
| 4,977,890 | A | 12/1990 | Mann | |
| 5,002,044 | A | 3/1991 | Carter | |
| 5,065,770 | A * | 11/1991 | Palfray | 600/587 |
| 5,316,547 | A | 5/1994 | Gildersleeve | |
| 5,385,536 | A | 1/1995 | Burkhead et al. | |
| 5,421,810 | A | 6/1995 | Davis et al. | |
| 5,437,619 | A | 8/1995 | Malewicz et al. | |
| 5,514,081 | A | 5/1996 | Mann et al. | |
| 5,545,162 | A | 8/1996 | Huebner et al. | |
| 5,683,353 | A | 11/1997 | Hamersly | |
| 5,707,370 | A | 1/1998 | Berki et al. | |
| 5,846,245 | A | 12/1998 | McCarthy et al. | |
| 5,916,184 | A | 6/1999 | McKeel | |
| 6,019,769 | A | 2/2000 | McCarthy et al. | |
| 6,179,799 | B1 | 1/2001 | Doran | |
| 6,589,195 | B1 | 7/2003 | Schwenn et al. | |
| 6,676,619 | B2 | 1/2004 | Arden | |
| 7,416,537 | B1 | 8/2008 | Stark et al. | |
| 7,476,207 | B2 | 1/2009 | Porrata et al. | |
| 7,645,279 | B1 * | 1/2010 | Haupt | 606/54 |
| 7,708,736 | B2 * | 5/2010 | Mullaney | 606/54 |
| 7,815,586 | B2 * | 10/2010 | Grant et al. | 602/23 |
| 8,147,491 | B2 * | 4/2012 | Lavi | 606/59 |
| 8,840,611 | B2 * | 9/2014 | Mullaney et al. | 606/59 |
| 2002/0035342 | A1 | 3/2002 | Williams | |
| 2004/0243038 | A1 * | 12/2004 | Patterson | 602/23 |
| 2005/0113831 | A1 * | 5/2005 | Franck et al. | 606/61 |
| 2005/0119656 | A1 * | 6/2005 | Ferrante et al. | 606/59 |
| 2007/0038217 | A1 * | 2/2007 | Brown et al. | 606/57 |

FOREIGN PATENT DOCUMENTS

| | | |
|---|---|---|
| FR | 2609887 A | 7/1998 |
| GB | 505775 A | 5/1939 |
| JP | 06335488 A | 12/1994 |
| WO | WO 94/23662 A | 10/1994 |
| WO | WO 2006/120482 A1 | 11/2006 |

OTHER PUBLICATIONS

International Search Report for corresponding PCT/GB2010/050289 completed May 10, 2010 by Peter Øen of the EPO.
International Search Report for corresponding PCT/GB2006/050102 completed Sep. 8, 2006 by Jean-Charles Assion of the EPO.

\* cited by examiner

FIXATOR

FIELD OF THE INVENTION

The present invention relates to a non-invasive external fixator particularly suitable for fracture fixation. Particular embodiments of the invention relate to an external fixator which allows for movement in a joint adjacent a fracture site; while certain embodiments relate to a fixator useful in movement, distraction and/or reduction of a fracture.

BACKGROUND OF THE INVENTION

When a bone is fractured, it is often necessary to hold the fragments of the bone together to allow for correct healing. If this is not done, problems such as misalignment or poor healing can occur.

A conventional means for fixing fracture fragments is an external fixator, which typically takes the form of a steel or other material rod spanning across the fracture which is fixed to the bone fragments using pins. The rod is located outside the body, while the pins penetrate the skin and are fixed in the bone. This invasive technique involves surgery, and as such there is a risk of infection of the soft tissue or bone, and further there is a risk of complications arising from the surgery.

A further disadvantage of conventional external fixators is where the fixator spans a joint, such as the wrist or ankle. The steel or other material rod may not be articulated, thereby preventing movement of the joint.

Articulated fixators are known, but these have disadvantages as well. Alignment of the articulation with the joint can be difficult if not impossible, due to articulation of the fixator not being in the plane of the joint line axis. Known devices do not allow movement in the joint's plane of motion. For example, the position of the articulation of the fixator is dependent on the position of the pins drilled in the bone which can only be drilled in a limited number of positions. Furthermore, known articulated fixators also have the disadvantage that if the fractured joints are moved in fracture situation, this will disturb the fracture position. In particular, known devices allow for multidirectional movement, including rotation, thereby allowing the fracture position to slip.

U.S. Pat. No. 4,677,971 discloses a wrist splint for the treatment of soft tissue injuries, as a splint after surgery or in fracture treatment of small bones of the wrist (carpal bones). However, the device does not have a bracelet comprising a plurality of elements arranged in a plurality of rows according to the present invention. Furthermore, as with other known devices, the device in U.S. Pat. No. 4,677,971 is not suitable for treating long bone fractures because the articulation piece is not at the fracture site or joint level and does not allow movement in the joint plane. The disclosure in WO 2006/120482, as incorporated herein by reference, also relates to a fixator or a splint.

In certain locations, such as for a fracture of the radial bone, the patient's thumb may prevent suitable alignment of the steel rod and the articulation. This problem has been addressed to a certain extent with ring external fixators, such as Ilazarov. However, such fixators necessitate a number of invasive pin placements and lead to a very big and cumbersome fixator.

Also known are casts that rely on a chemical reaction to change from a bandage (flexible) to cast (rigid) form in a reaction is irreversible. In contrast, the present invention provides a non-chemical, mechanical solution as the device provided can be adjusted from being flexible to being rigid in a reversible fashion.

It is an object of the present invention to obviate or alleviate these and other disadvantages of conventional fixators. It is a further object of the invention to provide a non-invasive external fixator, which permits movement of a joint near the fracture site and also allows for fracture reduction and aids fracture manipulation. The invention also provides a connecting device for the fixator of the invention. Connecting devices in the art are used to fix a rod or cylinder, i.e. a circular surface. Furthermore, the invention relates to a hinge suitable for use with a fixator. Hinges have been used in medical devices. However, these hinges have limitations to be used in fracture fixation device. These have traditionally been made of radiopaque materials such as metals and hence obscure the area of interest in fractures in radiographs (X-rays), see for example EP0676941 and EP0879032. It is very difficult to assess the centre of rotation of these hinges on radiographs and to ascertain whether these are in the plane of the joint motion. The present invention is aimed at addressing the shortcomings in the field.

SUMMARY OF THE INVENTION

The invention describes an external non-invasive fixator for fixing a fracture or soft tissue injury having at least two articulated bracelets. The invention also relates to the different parts of such a fixator as described herein, including the various embodiments of these parts as described. Disclosed are an articulated bracelet, a connecting device, a cross linking device, a hinge device, and a disengaging device which are all for suitable use with a non-invasive fixator for fixing a fracture or soft tissue injury as described herein.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Viewed from a first aspect, the present invention provides a non-invasive fixator for fixing a fracture or soft tissue injury comprising a first and a second articulated bracelet each bracelet comprising a plurality of elements arranged in a plurality of rows, wherein said elements have complementary linking means to permit linking said rows of elements together in an interchangeably articulated or fixed relationship, wherein one or more of said plurality of elements comprises means for receiving and engaging at least a portion of a connecting device such that the position of the connecting device can be altered around the bracelet or the limb that it is mounted on, at least one articulated connecting device on each of said first and second bracelet;

a rod connecting said at least one articulated connecting device on said first bracelet to said at least one articulated connecting device on said second bracelet and a hinge device.

In another embodiment, the fixator may comprise a third or more articulated bracelet.

Viewed from another aspect, the invention provides an articulated bracelet for an external non-invasive fixator for fixing a fracture or soft tissue injury as described herein, the bracelet comprising a plurality of elements arranged in a plurality of rows, wherein said elements have complementary linking means to permit linking said rows of elements together in an interchangeably articulated or fixed relationship, wherein one or more of said plurality of elements comprises means for receiving and engaging at least a portion of a connecting device such that the position of the connecting device can be altered around the bracelet or the limb that it is mounted on.

The preferred embodiments of the articulated bracelet according to the different aspects of the invention are set out below.

As used herein the term 'articulated relationship' refers to a relationship in which relative motion is allowed to occur, while 'fixed relationship' refers to a relationship in which relative motion is substantially restricted. It will be understood that in an articulated relationship there may be some degree of resistance to relative motion, for example sufficient for the articulated bracelet to holds its shape without sagging.

Thus, during assembly of the bracelet about a patient's limb for example, the elements can be linked in an articulated relationship to facilitate correct sizing. Once appropriately assembled, the elements can be fixed to provide support for the limb during the healing process. The bracelet can therefore be made to fit snugly around the patient's limb by adjusting its length and curvature in the process of fitting, without the need for straps or other encircling bands. The bracelets can be made substantially rigid by simple application of digital pressure on the built-in locking mechanism that involves engaging the elements of the bracelet. Stability is provided by virtue of using a plurality of rows of elements that can be made substantially rigid when conforming in appropriate shape around the limb. Thus, the bracelet according to the invention is capable of changing from a substantially rigid and fixed state to a flexible and articulated state. The bracelet and its elements can be manipulated to conform to the desired shape (circular, oval, etc) and length.

The non-invasive fixator may comprise two bracelets, one on either side of a fracture or soft tissue injury. Preferably, the fixator comprises three bracelets. To maintain the bracelets in relative positions, a connecting rod or the like can be used, which can be secured to the bracelets by connecting devices for example. One or more of the elements is therefore provided with means for receiving and engaging at least a portion of a connecting device.

In the context of the present invention, the term "connecting device" refers to any structure that can be used to connect one component to another component. Preferably, the connecting device can be received and engaged without the need for technical processing such as welding and soldering. An embodiment of an exemplary connecting device is described below, though it will be appreciated that other suitable connecting devices could also be used. The device is capable of being mounted on or secured to a flat surface/ rectangular/ square (bracelet side) and a cylindrical surface (the rod side). The connectors are preferably made of metal but are away from the fracture site.

In preferred embodiments of the articulated bracelet, the elements of adjacent rows are offset relative to one another in a row direction. Preferably, the bracelet comprises a central row of elements and two outer rows of elements, in which one or more elements of the central row can have the means for receiving and engaging at least a portion of a connecting device. This again provides stability.

In preferred embodiments the means for receiving and engaging comprises a channel, which can be partially enclosed by inwardly extending segments. The connecting device can be snapped, pressed, turned or otherwise inserted into the channel. However, in preferred embodiments the channel has at least one open end so that the connecting device can be slid into the channel. This enables quick assembly of the bracelet, yet also allows for secure engagement with the connecting device. To facilitate easier insertion of the connecting device, the inwardly extending segments can have bevelled corners at the at least one open end. Further, the channel can extend substantially along the entire length of the element in which it is defined.

The elements have complementary linking means to permit linking the rows of elements together in an interchangeably articulated or fixed relationship. Preferred embodiments are described below, although other embodiments, such as hinges, pins and hook also within the scope of the invention.

The linking means provide a mechanism by which the position of one row of elements with respect to the adjacent row of elements can be adjusted and fixed or locked in the desired position. This way, the curvature of the bracelet can be adjusted. Once in the desired position, the relationship can be fixed so that the position does not change unless the linking mechanism is unlocked. This way, the healing process is not jeopardised as the patient cannot inadvertently tamper with the bracelet.

In one embodiment, the linking means can comprise at least one arcuate projection extending laterally to the row direction on a first of the elements, and at least one arcuate slot for receiving the arcuate projection in a second of said elements, where the first and second elements belong to adjacent rows. Broadly speaking, the arcuate nature of the projection and slot means that a range of relative positions can be adopted. Although the arcs of the projection and the slot can be substantially equal, for example substantially circular (i.e. cylindrical), in preferred embodiments the arc of the slot is greater than the arc of the projection. For example, the arc of the arcuate slot can be that of a semicircle while the arc of the projection can be that of a quarter of a circle. This can usefully limit the range of relative rotation, for example to ensure that the bracelet is assembled correctly.

It will be appreciated that the projection and slot can be engaged in a fixed relationship in a number of different ways. However, in a preferred embodiment, a first arcuate surface of the arcuate projection is provided with one or more ridge-like teeth extending laterally to the row direction. The teeth can extend laterally only part way along said projection, so that the slot can guide the (partially inserted) arcuate projection to a desired position before being fixed. In preferred embodiments, a first arcuate surface of the slot is provided with one or more ridge-like teeth extending laterally to the row direction. It will be appreciated that the number, and positioning, of the ridge-like teeth can be varied.

In preferred embodiments, a second arcuate surface of the arcuate projection is provided with one or more arcuate grooves. In preferred embodiments a second arcuate surface of said slot is provided with a latch extending laterally to said row direction.

Broadly speaking, the ridge-like teeth of the projection and slot serve to hinder relative rotational movement, while the groove and latch arrangement help to hinder relative lateral movement. Alternatively, or additionally, relative lateral movement may be hindered by frictional engagement between the slot and projection. For example, the arcuate projection could be held by a narrowing slot, either or both of which could be comprised of resiliently deformable material. Of course, other means of linking elements together, such as pins, hook, and hinges, could also be utilised, provided that the means allow linking together in an articulated or fixed relationship.

In preferred embodiments, the plurality of elements comprise first and second kinds of elements, the first kind of elements having a plurality of arcuate projections and the second kind of elements having a plurality of slots. For convenience, throughout the description, elements of the first kind which have a plurality of arcuate projections will be referred to as "tabbed elements", and elements of the second kind which have a plurality of slots will be referred to as "slotted elements". It will be understood, however, that the term "tabbed element" is intended to refer to any element having a projection that can be received by a slot, while the term "slotted element" is intended to refer to any element having a slot that can receive a projection. Elements are not limited to having either projections or slots, and could have both.

In preferred embodiments, the first kind of elements has four arcuate projections and the second kind of elements has two slots. In preferred embodiments, substantially all of the elements of a given row are of the first kind or the second kind of element. Thus, for example, the central row can comprise a plurality of elements of the first kind and the two outer rows can comprise a plurality of elements of the second kind.

In preferred embodiments the plurality of elements is made of rigid, radiolucent and resilient material, for example a plastic material. The material used is also waterproof. The underside of the material may be lined with a non rigid, breathable material to increase wearing comfort.

Preferably the elements of the bracelet can be linked together by hand without the use of tools to achieve a fixed relationship of the elements with respect to each other. Thus, for example, the bracelet can be made rigid or articulated by simple finger (digital) pressure. Preferably, as in the embodiments described herein, once in a fixed relationship, the linking means cannot be easily undone by hand. This results in a tamper-free bracelet and prevents the patient from inadvertently adjusting the bracelet. Preferably, a disengagement tool is needed (detailed below) to help to unlink the elements.

In preferred embodiments, the articulated connecting device of said external non-invasive fixator comprises a pair of clamp members, each member having a channel that can be aligned in opposed relationship with one another to form a hole for receiving a rod, at least one of said pair of clamp members having a part-spherical portion for mating with a complementary part-spherical portion of a support member, said support member being mountable on, or integral with, a spacer portion of a base, wherein said pair of clamp members, said support member and said base are releasably secured together, for example by a pin, and wherein said device is capable of being mounted on a flat surface, rectangular or square and a cylindrical surface. Further embodiments of the articulated connecting device are set out below.

In another aspect of the invention there is provided an articulated connecting device for an external non-invasive fixator, the connecting device comprising a pair of clamp members, each member having a channel that can be aligned in opposed relationship with one another to form a hole for receiving a rod, at least one of said pair of clamp members having a part-spherical portion for mating with a complementary part-spherical portion of a support member, said support member being mountable on, or integral with, a spacer portion of a base, wherein said pair of clamp members, said support member and said base are releasably secured together for example by a pin, and wherein said device is capable of being mounted on a flat surface, rectangular or square and a cylindrical surface.

Broadly speaking, the complementary part-spherical portions of the clamp and support member of the connecting device form a universal joint allowing relative rotational and tilting movement. Thus, the pair of clamp members is capable of moving in all planes. However, the position of the pair of clamp members can also be fixed.

In preferred embodiments, the channel is offset from a central axis of said coupling device, so that the pin runs centrally through the components. In preferred embodiments the base is slidably receivable in a channel of an element of the aforementioned bracelet.

The fixator may also comprise a cross-linking device. In a preferred embodiment, the cross-linking device comprises first and second pairs of clamp members, each member having a channel that can be aligned in opposed relationship with the channel of its paired member to form a hole for receiving a rod, said first and second pairs being releasably secured together back-to-back by a pin. Further embodiments of the cross-linking device are set out below.

In yet another aspect of the invention there is also provided a cross-linking device for a non-invasive fixator, the cross-linking device comprising first and second pairs of clamp members, each member having a channel that can be aligned in opposed relationship with the channel of its paired member to form a hole for receiving a rod, said first and second pairs being releasably secured together back-to-back by a pin.

In preferred embodiments, each of the channels is offset from a central axis of the cross-linking device.

The fixator also comprise a hinge device. In preferred embodiments, said hinge device comprises a first hinge part having a pair of spaced first and second ring members; a second hinge part having a third ring member pivotably accommodated between said first and second ring members, said third ring member having inwardly directed teeth formed on an inner circumferential surface thereof; a third hinge part comprising first and second cylindrical members extending through said first and second ring members respectively, each of said first and second cylindrical members have outwardly directed teeth formed on an outer circumferential surface thereof, for engaging with said inwardly directed teeth of said third ring member; and a pin for releasably securing together said first, second and third hinge parts wherein said members are made of substantially radiolucent material and said pin is made of substantially radiopaque material and wherein the hinge permits movements in all planes. Further embodiments of the hinge device are set out below.

In yet another aspect of the invention, there is also provided a hinge device for a non-invasive fixator for fixing a fracture or soft tissue injury, the hinge comprising: a first hinge part having a pair of spaced first and second ring members; a second hinge part having a third ring member pivotably accommodated between said first and second ring members, said third ring member having inwardly directed teeth formed on an inner circumferential surface thereof; a third hinge part comprising first and second cylindrical members extending through said first and second ring members respectively, each of said first and second cylindrical members have outwardly directed teeth formed on an outer circumferential surface thereof, for engaging with said inwardly directed teeth of said third ring member; and a pin for releasably securing together said first, second and third hinge parts wherein said members are made of substantially radiolucent material and said pin is made of substantially radiopaque material and wherein the hinge permits movements in all planes.

Embodiments of the hinge device according to the different aspects of the invention are set out below.

Hinges typically used in medical devices are made of radiopaque materials. In the present hinge radiolucent material is used, except for the central pin, which is radiopaque. This allows visualisation of the fracture area and the metal pin identifies the centre of rotation of the hinge that has to be lined up with the centre of rotation of the joint. This is facilitated by the fact that when this pin in centre of the hinge is looked end-on, in a lateral radiograph, the pin will appear as a dot. Same pin looked from above, in an antero-posterior radiograph, will appear as a 'radiopaque line' but it will be visible outside of the fracture zone as it lies outside the limb and not implanted in. When both the line and the dot appear in a line projected to go through the centre of the joint on a radiograph, the axes of the hinge and the joint will be lined up.

Setting up the range of movement has been difficult with the presently available hinges as they necessitate a tool and/or metal pins to achieve that. The hinge described here allows the range of motion to be controlled digitally by the person applying the hinge and it can be read from the numbers inscribed on the two discs. The person applying the hinge can pull it apart by couple of mm with his fingers on the two discs on either side of the hinge and the numbers inscribed on the discs guide him to choose optimal position, say 15 degrees on one side and 45 degrees on the other. He then pinches the two discs together to secure that position. In addition, to make it tamper proof, the central pin or bolt can be locked using a slotted key.

In preferred embodiments of the different aspects of the invention, the first, second and third hinge parts are provided with means for selectively limiting the range of pivoting movement of the second hinge part relative to the first hinge part. Thus, the hinge can be made rigid (i.e. no movement) or a selective range of motion can be provided (e.g. within a 180 degree arc, such as from 30 degrees to 45 degrees). In a preferred embodiment, the hinge or articulation member allows all-plane movement and distraction.

As mentioned above, numbers inscribed on the two discs facilitate setting up the range of movement.

In yet another aspect of the invention, there is provided an element for an articulated bracelet as described herein for use with an external non-invasive fixator for fixing a fracture or soft tissue injury as described herein, the element comprising a first kind of element having linking means to permit linking to a second kind of element in an articulated or fixed relationship, said first kind of element comprising a body defining a channel, said channel being partially enclosed by inwardly extending segments and having at least one open end, each of said arcuate projections having one or more laterally extending ridge-like teeth on a first arcuate surface.

Preferably, each of the arcuate projections is provided with one or more arcuate grooves in a second arcuate surface.

In yet another aspect of the invention, there is provided an element for an articulated bracelet as described herein for use with an external non-invasive fixator for fixing a fracture or soft tissue injury as described herein, the element comprising a second kind of element having linking means to permit linking to a first kind of element in an articulated or fixed relationship, said second kind of element comprising a body defining two side-by-side, semi-circular slots, each of said slots having one or more laterally extending valleys in a first arcuate surface.

Preferably each of the slots is provided with a laterally extending catch in a second arcuate surface.

In a related aspect of the invention, there is provided a method of treating a fracture, the method comprising securing a non-invasive fixator to a patient's limb, wherein the fixator comprises: at least first and a second aforementioned bracelet; at least one aforementioned connecting device on each of said first and second bracelet; and a rod connecting a said at least one connecting device on said first bracelet to a said at least one connecting device on said second bracelet.

The device of the invention is suitable for fixing a fracture. The term fracture includes a fracture of the long bones. In one embodiment, the fixator of the invention is used to treat long bone fractures. The device can be used during all stages of fixing the fracture, including for fracture reduction (moving the broken pieces of bone to normal configuration), fracture manipulation (moving fracture fragments) and treating fractures in such a fashion that the joint in proximity can be mobilised wile maintaining the fracture position immobilised.

The fixator is particularly useful in first aid methods when access to a hospital is not available as it can be readily applied. Furthermore, the fixator allows access to skin at the fracture site where local treatment, such as cryotherapy, may be applied. This is particularly important in fractures where significant soft tissue swelling ensues, such as ankle fractures. The fixator also allows for soft tissue access and wound care in postoperative cases.

As described above, the fixator described herein is particularly suitable for fracture fixation. Furthermore, the fixator described herein may also be used for soft tissues corrections and treatment of deformities. The articulations may provide the means for repeated adjustments. This is normally done by serial plaster casting which is time consuming and uncomfortable for the patient. The use of the fixator provides the advantage that it can be adjusted and allows movement of the joint. Thus, in yet another related aspect of the invention, there is provided a method of treating soft tissue injuries, the method comprising securing a non-invasive fixator to a patient's limb, wherein the fixator comprises: a first and a second aforementioned bracelet; at least one aforementioned connecting device on each of said first and second bracelet; and a rod connecting a said at least one connecting device on said first bracelet to a said at least one connecting device on said second bracelet.

Furthermore, the fixator described herein may be used after surgical procedures, which may comprise procedures on the bone or soft tissues or combination of both. These procedures may be for emergency or elective surgery where a certain position of the limb is to be maintained with or without allowing movement across the adjacent joint.

The present invention allows for bone fragments to be maintained in position during healing. The hinge member and connecting device permit movement between the two bracelets of the fixator, such that the patient is able to flex a joint or move a limb in the vicinity of the fracture to alleviate fatigue and reduce stiffness while still retaining the fracture fragments in alignment. Further, the fixator is non-invasive and hence there is no risk of infection or complications of invasive surgery. Being non-invasive, the fixator can be placed in such a fashion that the plane of movement of the joint is in line with the plane of movement of articulating segment of the device, so minimising the chances of disturbing the position of fracture fragments when the joint is mobilised, improving patient comfort and healing. With invasive pin fixators, such positioning is difficult to achieve because placement of the pins is constrained by the presence of the thumb, vital structures or other members of the limb.

The fixator may also be used in veterinary surgery.

In a further embodiment of the invention, the fixator may also be provided as a kit of parts for assembly.

In yet another aspect of the invention, there is provided a disengaging device for disengaging elements of an articulated bracelet as described herein having a plurality of elements as described herein arranged in a plurality of rows, the rows of elements being linked together in a fixed relationship, the disengaging device comprising: an elongated body having a head portion at one end; and first and second handle members each having a grip portion and a jaw portion; wherein said first and second handle members are pivotally connected to opposite sides of said elongated body, so that when said grip portions move towards each other said jaw portions move away from each other.

In a related aspect of the invention, there is provided a method of disengaging elements of an articulated bracelet as described herein having a plurality of elements arranged as described herein in a plurality of rows, the rows of elements being linked together in a fixed relationship, the disengaging device having: an elongated body having a head portion at one end, and first and second handle members each having a grip portion and a jaw portion, wherein said first and second handle members are pivotally connected to opposite sides of said elongated body, so that when said grip portions move towards each other said jaw portions move away from each other, the method comprising: placing said head portion of said elongated body and said jaw portions of said first and second handle members between two adjacent elements of a first row of said plurality of rows; and pressing said grip portions of said first and second handle members towards each other so that said jaw portions push against elements belonging to rows adjacent to said first row.

In yet another aspect of the invention there is provided an articulated bracelet, a connecting device, a cross linking device, a hinge, a disengaging device and a non-invasive fixator as substantially described herein with reference to the drawings.

The fixator preferably does not comprise any resilient materials (springs and the like). The hinge member articulates at the level of the joint line and at the level of the fracture. The ability to articulate at the two levels enables the device to reduce fracture fragments and mobilise the wrist. The device thus permits movement of a joint near the fracture site and also allows for fracture pieces to be manipulated and reduced in position and yet allows mobilisation in the joint plane. Therefore, the device aids fracture manipulation whilst allowing the patient to move the joint. In one embodiment, the fixator is for treating long bone factures.

In one embodiment, the fixator comprises a lining material.

BRIEF DESCRIPTION OF THE DRAWINGS

These and other aspects of the present invention will now be described by way of example only and without limitation with reference to the accompanying drawings in which.

DETAILED DESCRIPTION OF PREFERRED EMBODIMENTS

Figure 1:
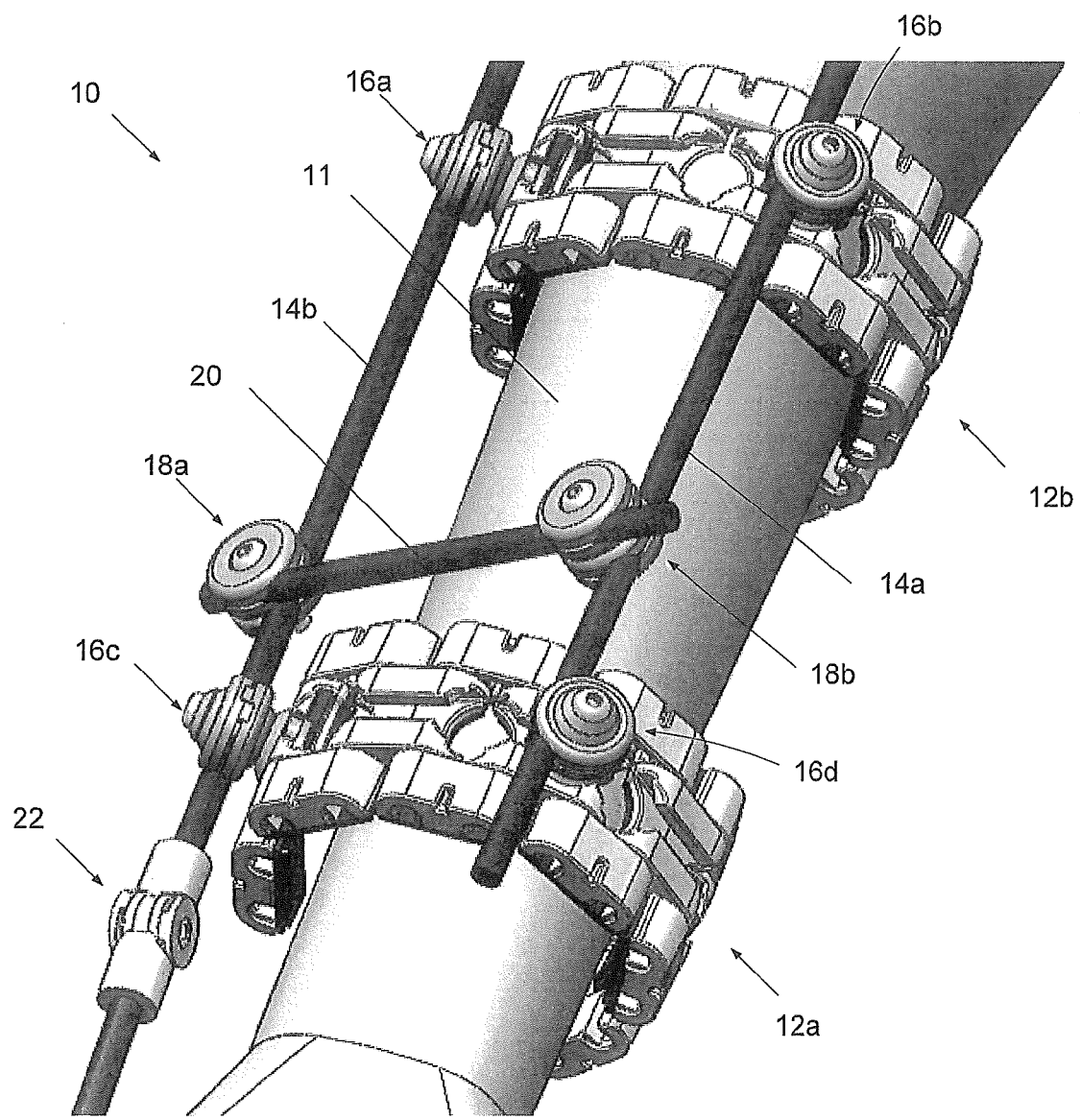
FIG. 1 shows a perspective view of a fixator in accordance with an embodiment of the invention mounted on a patient's arm.

FIG. 1 shows a non-invasive fixator 10 according to the present invention, mounted on an arm 11 of a patient. The fixator 10 comprises two bracelets 12a, 12b that are maintained in relative positions on the arm by two approximately parallel running rods 14a, 14b, which are secured to the bracelets by means of four connecting devices 16a, 16b, 16c, 16d (two at each bracelet). A third rod 20 is secured crosswise by two cross-linking devices 18a, 18b. A hinging device 22 is connected at one end of rod 14b. The hinge device is connected by means of a rod to another bracelet or a cuff (not shown). Thus, in a preferred embodiment, the fixator comprises three bracelets. The hinge device is aligned with the plane of the joint, adjacent to fracture zone, movement.

The bracelets 12 are comprised of a plurality of elements arranged in rows. In the exemplary configuration shown in FIG. 1, the elements are arranged in three rows: a central row and two outer rows. This is illustrated in more detail in FIG. 2, which shows a portion of a bracelet in an almost assembled state. Here, the central row is comprised of elements 24 having projections 48 (named "tabbed elements" for convenience) with the two outer rows being comprised of elements 26 having slots 62 (named "slotted elements" for convenience).

Figure 2:
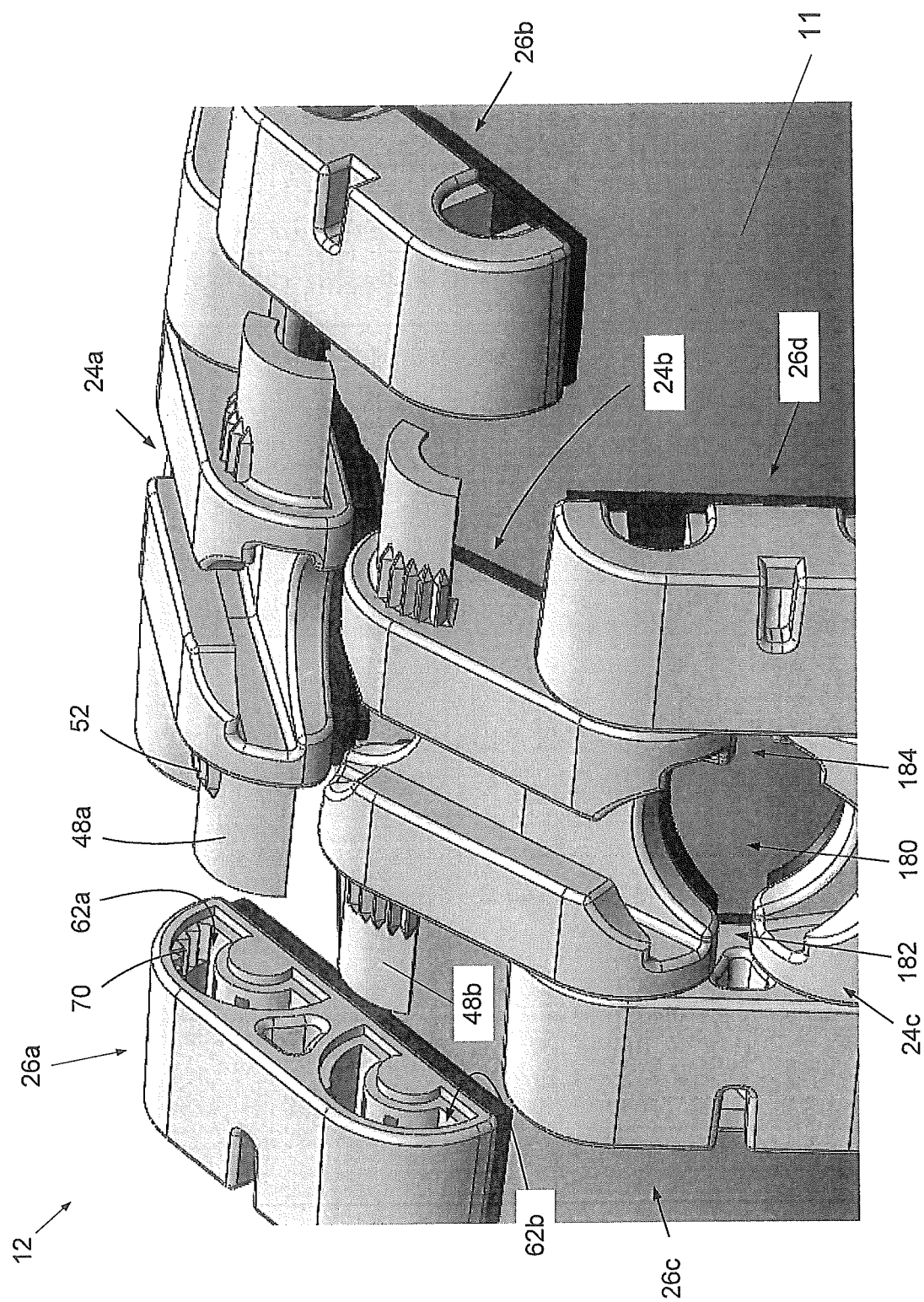
FIG. 2 shows a detail of a bracelet, in an almost assembled state, in accordance with an embodiment of the invention.

In FIGS. 1 and 2, each element of the central row links to two elements of the each of the adjacent outer rows, so that elements of adjacent rows are offset relative to one another. Thus, tabbed element 24b is in a fixed articulated relationship with slotted element 26c of the left-hand outer row and slotted element 26d of the right-hand outer row, and is about to be linked to slotted elements 26a and 26b, to complete the left- and right-hand outer rows.

Visible in FIG. 2 are the ridge-like teeth 70 formed on an inner arcuate surface of slot 62a of element 26a, for engaging with ridge-like teeth 52 on an upper arcuate surface of projection 48a of element 24a. These and other exemplary features of the tabbed and slotted elements will be described in due course. Here, it is briefly noted that the ridge-like teeth 70, 52 are complementary and when engaged with each other permit elements 26a and 24b to be linked in a fixed relationship. This is discussed in more detail below with reference to FIGS. 7a to 7f.

Figure 3:
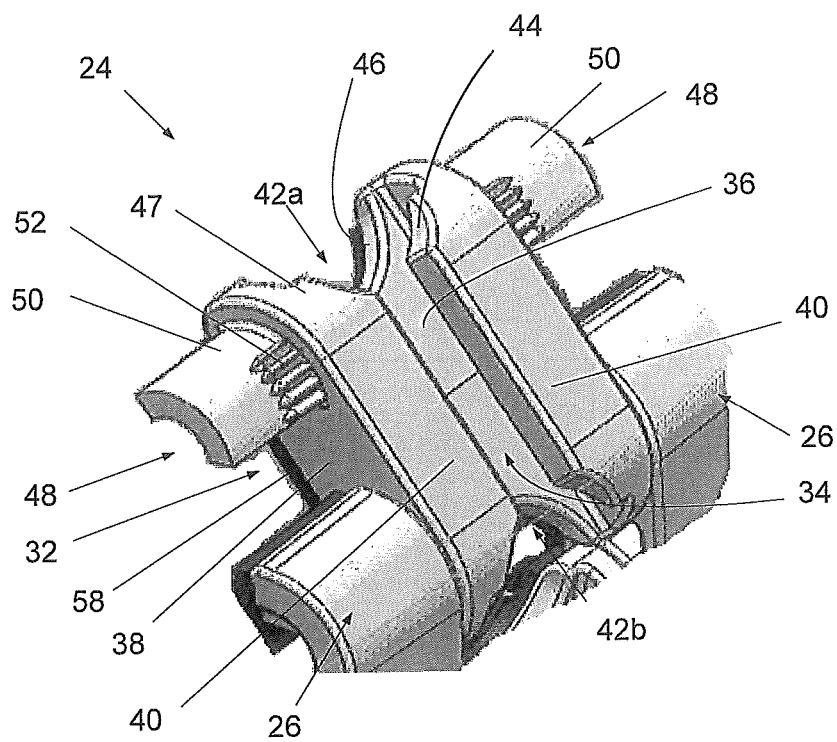
FIGS. 3 and 4 show top and bottom perspective views of a first kind of linkable element in accordance with an embodiment of the invention.
Figure 4:
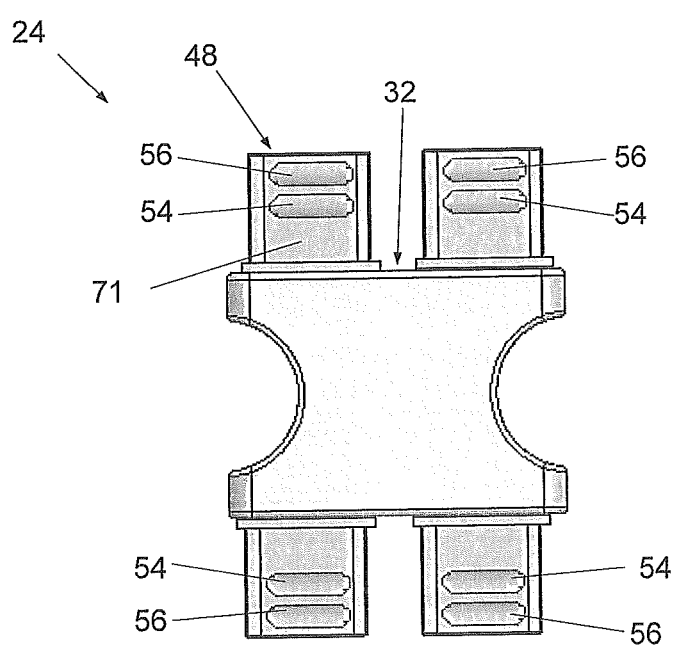

Turning first to FIGS. 3 and 4, which show element 24 from above and below, the element 24 has a body 32 that defines a channel 34 of rectangular cross-section. The channel 34 has a flat base 36 and parallel, upstanding sidewalls 38 having integral, inwardly extending segments 40 which overhang the base 36 and partially enclose the channel. In this particular example, the gap between the segments extends substantially along the entire length of the channel, which is open at both ends 42a, 42b. The segments have bevelled corners 44, which permit easier insertion of a connecting device (not shown; described later) into the channel, and rounded shoulders 47, which permit placing of jaws of a disengaging device (not shown; described later). The base has curved ends 46.

In the exemplary element 24 shown here, four arcuate projections 48 extend laterally at the longitudinal ends of sidewalls 38. Two of the arcuate projections are obscured from view by elements 26 in FIG. 3. The projections 48 cover an approximate ninety-degree arc, from an upper to a lower portion of the sidewalls, with arcuate surfaces 50 concaved upwards. A plurality (five in this case) of parallely arranged, ridge-like teeth 52 extend from the sidewall, part way along the lateral width of the upper arcuate surface 50, and also part way along the arcuate length of upper arcuate surface 50. As shown in FIG. 4, an inner and an outer arcuate groove 54, 56 are formed on the second, bottom arcuate surface 71 of projections 48. Foam 58, or other cushioning, can be provided on the bottom of the body 32.

Figure 5:
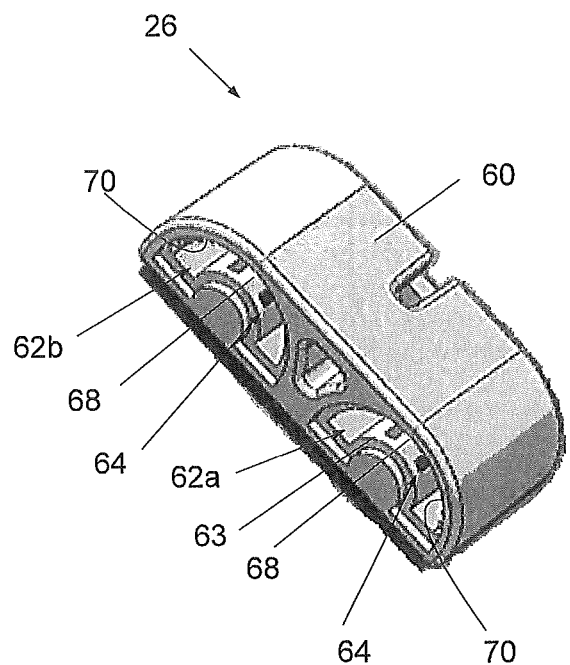
FIGS. 5 and 6 show top and bottom perspective views of a second kind of linkable element in accordance with an embodiment of the invention.
Figure 6:
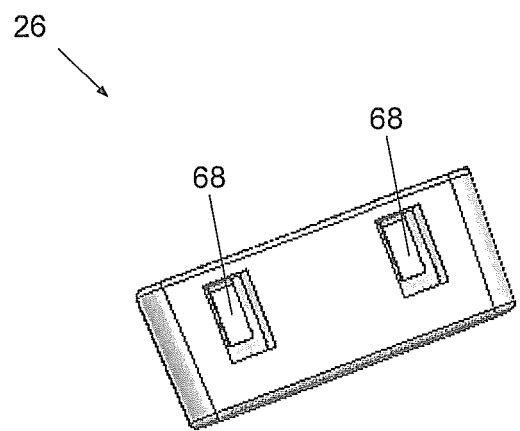

Referring now to FIGS. 5 and 6, element 26 has a body 60 in which two semi-circular slots 62a, 62b are defined. Each slot 62 has a lower arcuate surface 63, and an upper arcuate surface (not visible in FIG. 5) that has a greater radius of curvature. The lower arcuate surface 63 features an integrally defined latch 68 (partially hidden from view in FIG. 5), with the upper arcuate surface featuring a plurality of parallely arranged, ridge-like teeth 70 extending inwardly from the opening of the slots.

The latches 68 extend inwardly in the same direction as the ridge-like teeth 70, with a tip at one end for engaging the outer and inner arcuate grooves 56, 54 of the projection 48 of element 24 (FIG. 4). Viewed from beneath (FIG. 6), a portion of the body is removed from below each of the slots to allow the latch to move up and down.

Figure 7A:
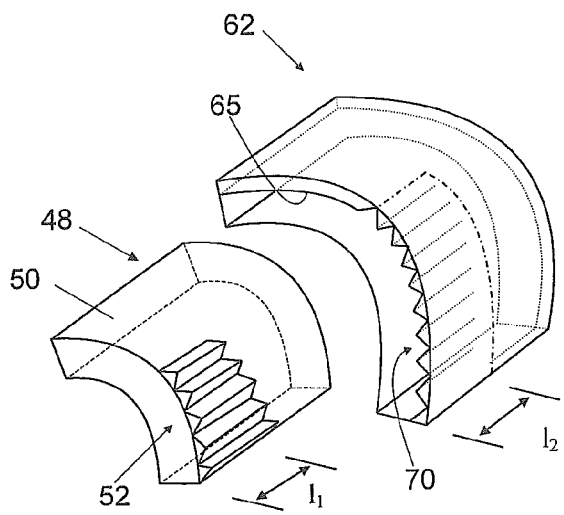
FIGS. 7a to 7f show three different states of a complementary linking means in accordance with an embodiment of the invention.
Figure 7B:
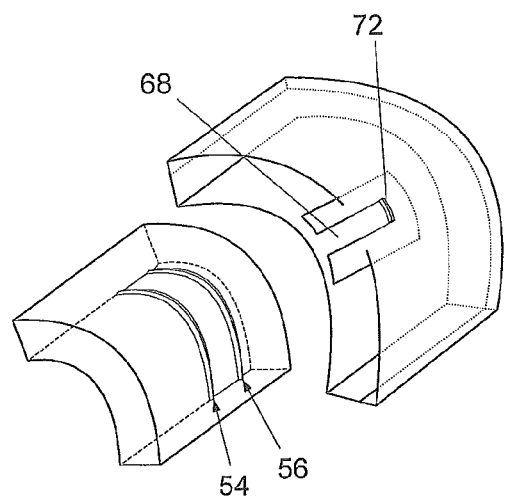
Figure 7C:
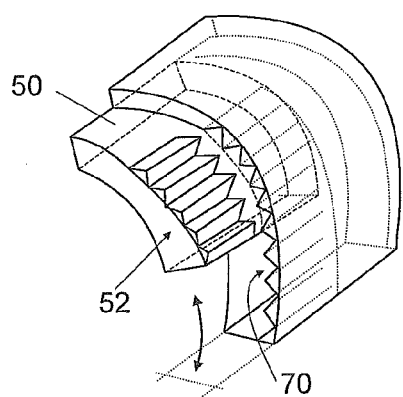
Figure 7D:
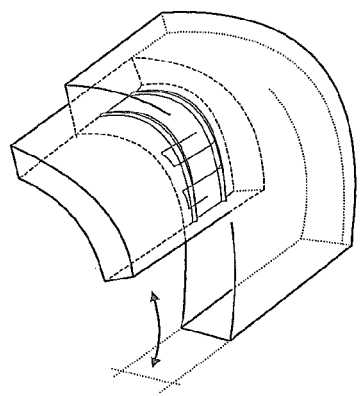
Figure 7E:
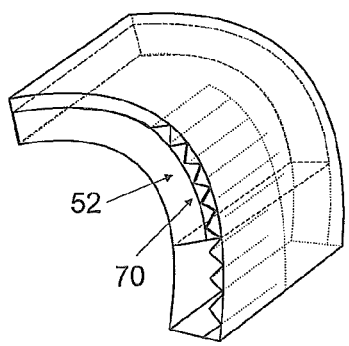
Figure 7F:
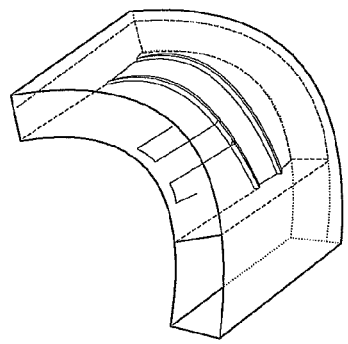

FIGS. 7a to 7f show three different 'link states' of an arcuate projection 48 and slot 62 for receiving the projection: unlinked (FIGS. 7a and 7b); linked to permit relative movement (FIGS. 7c and 7d); and linked in a fixed relation (FIGS. 7e and 7f). Left- and right-hand figures correspond to one another, but for clarity details of the two sets of ridge-like teeth and latch-and-groove are separated.

In FIG. 7a, the lateral length, $l_1$, of the ridge-like teeth 52 of the arcuate projection 48 is approximately the same as that the depth to which the ridge-like teeth 70 of the slot extend inwards, $l_2$ (indicated by the dashed-dotted line). Further, the arcuate distance covered by the ridge-like teeth 70 of the slot can be greater than the arcuate distance covered by the ridge-like teeth 52 of the projection 48 of the tabbed element 24. In other configurations, however, either or both of the ridge-like teeth 52, 70 could cover different areas of the respective surfaces. FIG. 7b shows the grooves 54, 56 of the arcuate projection and the latch 68 with tip 72 of the slot 62.

In FIG. 7c, the arcuate projection 48 is partially inserted into the slot 62, such that the ridge-like teeth 52, 70 almost engage with each other. As seen in FIG. 7d, the outer groove 56 is positioned so that when this changeable relationship is reached, the tip of the latch 68 engages therewith. The slot can thus rotationally guide the arcuate projection until a desired position is reached, while minimising relative lateral displacement during the positioning process, and can be of use where a number of linkable elements are being positioned before being linked together in a fixed relationship.

In FIG. 7e, the arcuate projection is fully inserted into the slot such that the two sets of ridge-like teeth 52, 70 mesh with each other, thereby hindering any further rotation. As can be seen from these Figures, the relative arrangement of the two sets of teeth 52, 70 can be such that all of the teeth 52 of the arcuate projection can be engaged, irrespective of the relative articulated position. The inner groove engages with the tip of the latch when the elements are in this fixed articulated relationship (FIG. 7e).

Figure 8:
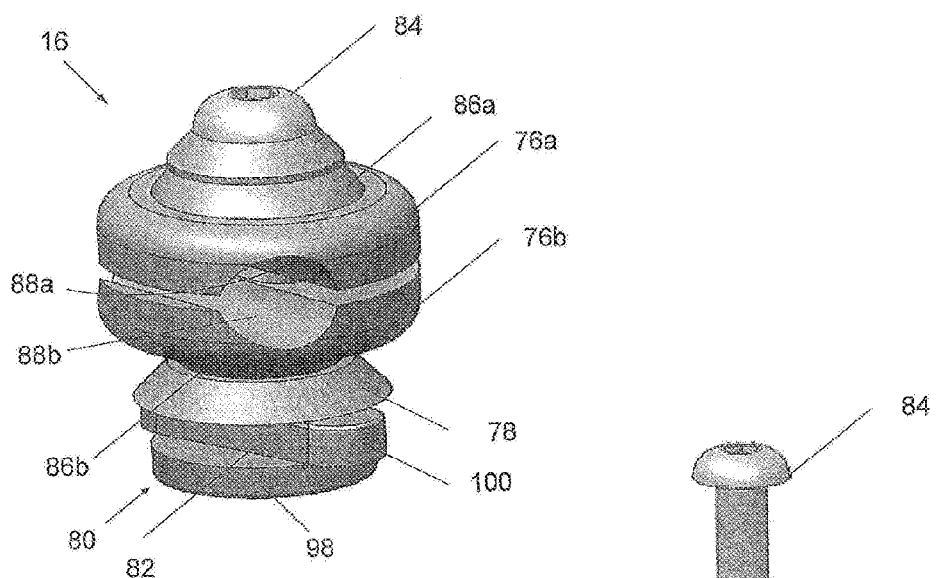
FIGS. 8 and 9 show assembled and exploded perspective views of a connecting device in accordance with an embodiment of the invention.
Figure 9:
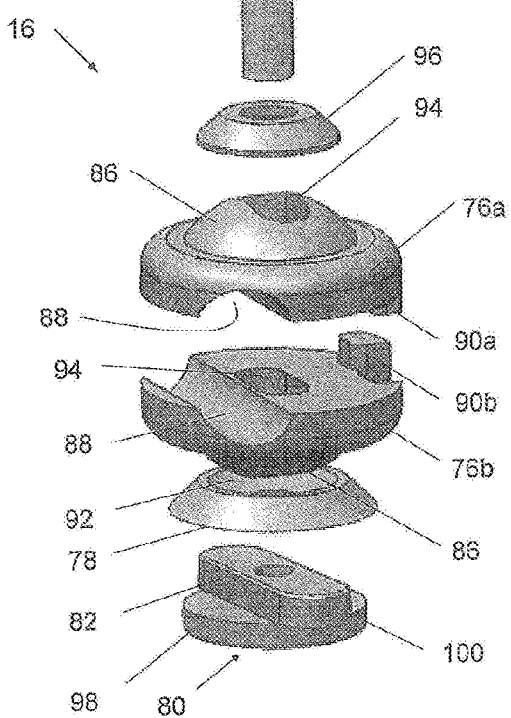

FIGS. 8 and 9 show an exemplary connecting device 16, in assembled and exploded views respectively. The device 16 comprises a pair of clamping members 76a, 76b, a cup-like supporting member 78, and a base 80. The components can be secured together by a pin 84, which may have a threaded end (not detailed).

In this example, the clamping members 76a, 76b are substantially identical, and are formed as disc-shaped pieces. A part-spherical projection 86a, 86b is formed on one side of each of the clamping members 76a, 76b, while the other side features a channel 88a, 88b. When clamped together, the channels define a hole, to allow a rod or other object to be clamped therebetween. The channels are offset from centre, to allow the pin 84 to pass centrally. Two blocks 90a, 90b project from the surface and coupled together hinder relative rotation of the clamp members.

The part-spherical projections 86 of the clamp members, which here are concave protrusions, complement the convex part-spherical portion 92 of the supporting member 78. This forms a universal-type joint that allows the clamping members to be rotated and inclined. Oblong holes 94 in the clamping members, together with a washer 96, allow the pin 84 to remain substantially vertical when the clamp members are tilted forwards or backwards.

The supporting member 78 sits on a spacer 82, which separates the disc-like portion 98 of the base 80 from the supporting member 78. The spacer 82, which can receive the threaded end of the pin 84, is elongated across a diameter of the disc and has rounded ends 100.

Figure 10:
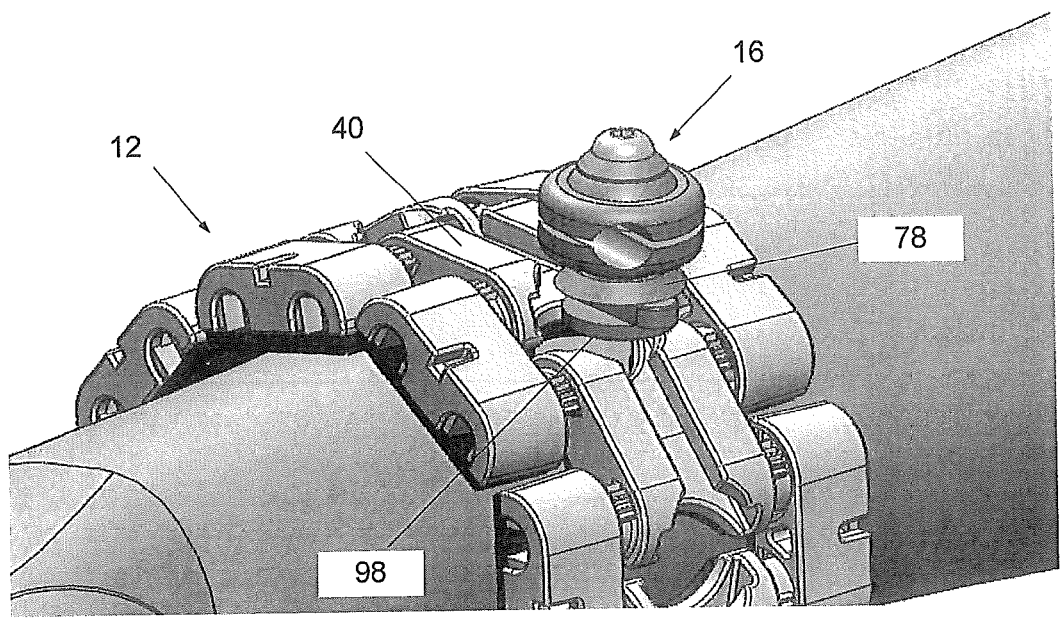
FIGS. 10 and 11 show details of a bracelet and a connecting device in accordance with embodiments of the invention, before and after the connecting device is mounted on the bracelet.
Figure 11:
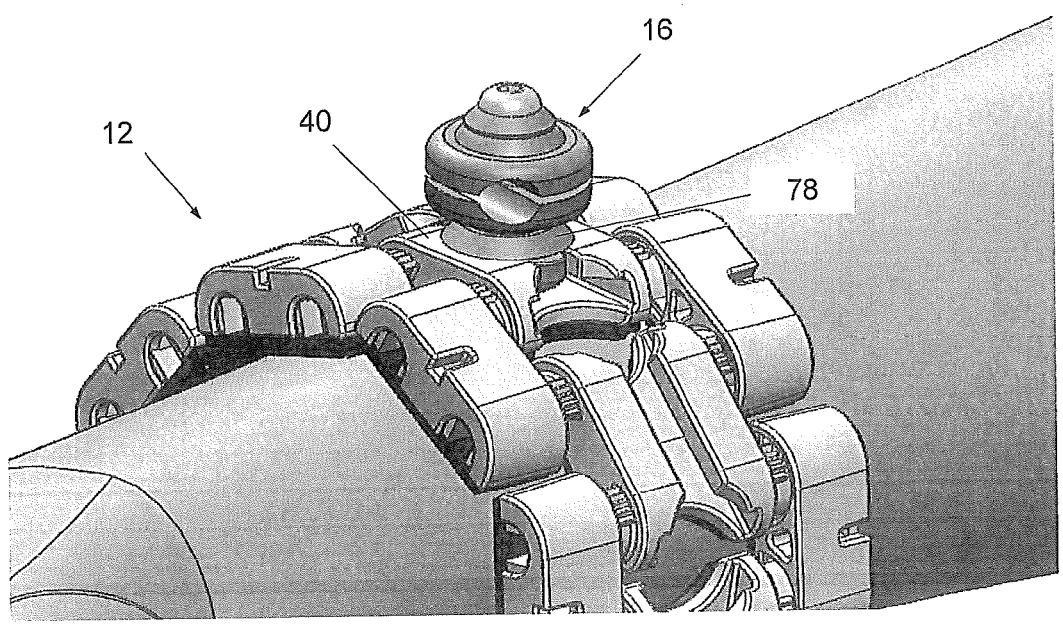

FIGS. 10 and 11 show how a connecting device 16 can be mounted on a bracelet 12, after the bracelet has been assembled (though a connecting device could equally be mounted before assembly or can even be integral with a linkable element). The disc-like portion 98 of the base 80 slides into the channel of element 24 from an open end, underneath the inwardly extending segments 40, which receive the elongated spacer therebetween. The supporting member 78 resides above the segments 40. The pin can at first loosely bind the various components of the connecting device, and then be screwed tight so that the supporting member 78 and base 80 securely grip the inwardly extending segments 40, thereby engaging the connecting device 16 to the bracelet element.

Figure 12:
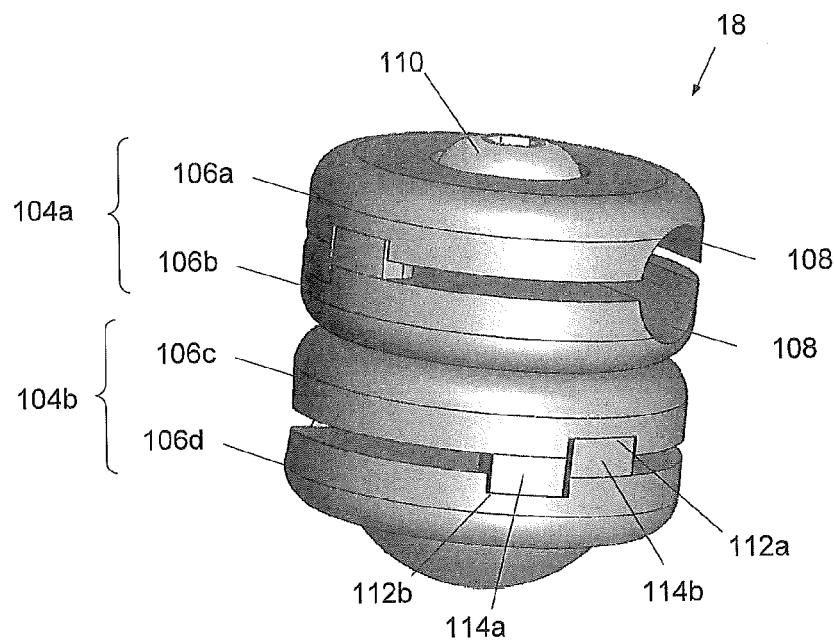
FIGS. 12 and 13 show assembled and exploded perspective views of a cross-linking device in accordance with an embodiment of the invention.
Figure 13:
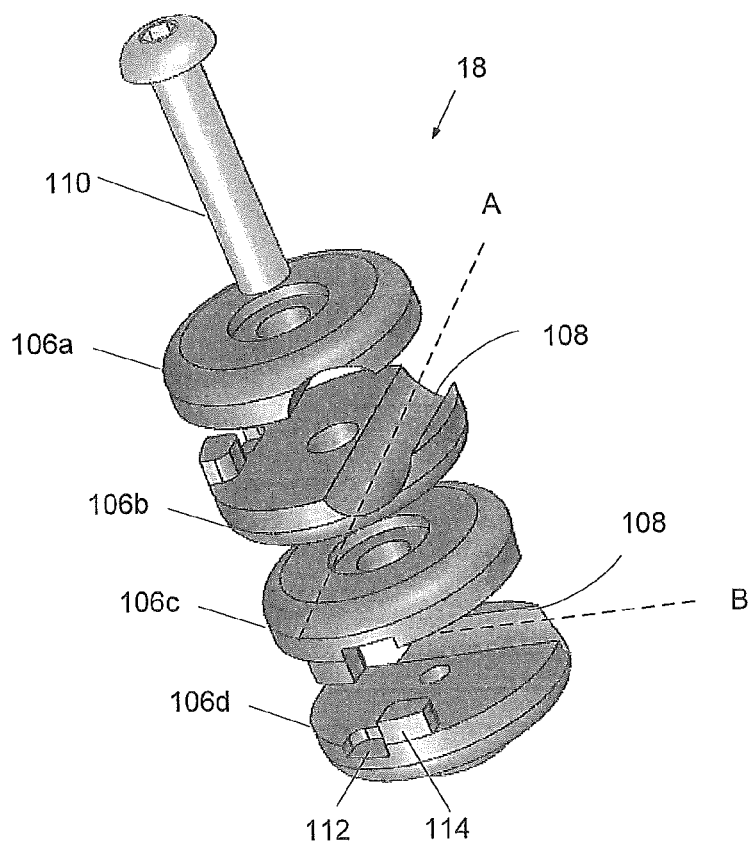

FIGS. 12 and 13 depict an exemplary cross-linking device 18, in assembled and exploded views respectively. The device comprises four clamping members 106a, 106b, 106c, 106d arranged as two clamps 104a, 104b. These clamping members can have features in common with the clamping members of the connecting device 16, such as being generally disc shaped and having channels 108 (only two channels can be seen in FIG. 12), though having at least one flat side allows two clamping members 106b, 106c to be mounted back-to-back. Also, each member has an indent 112 and adjacent notch 114 on a periphery of the disc structure, which can be mated with those of the member with which it is paired (e.g. 114a, 112b; 114b, 112a). A pin, which can have a threaded end (not shown), is used to fasten the components together. The clamps 104a, 104b can be rotated relative to one another so that the rods can be directed in different relative orientations. For example, FIG. 13 shows bores at a ninety degree angle relative to one another (indicated by dashed lines A and B).

Figure 14:
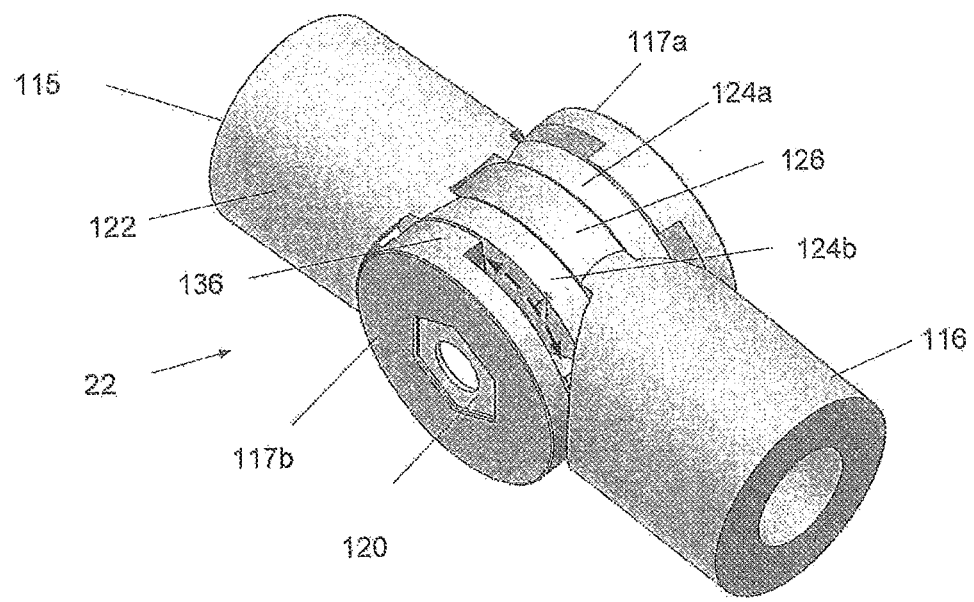
FIGS. 14 and 15 show assembled and exploded perspective views of a hinging device in accordance with an embodiment of the invention.
Figure 15:
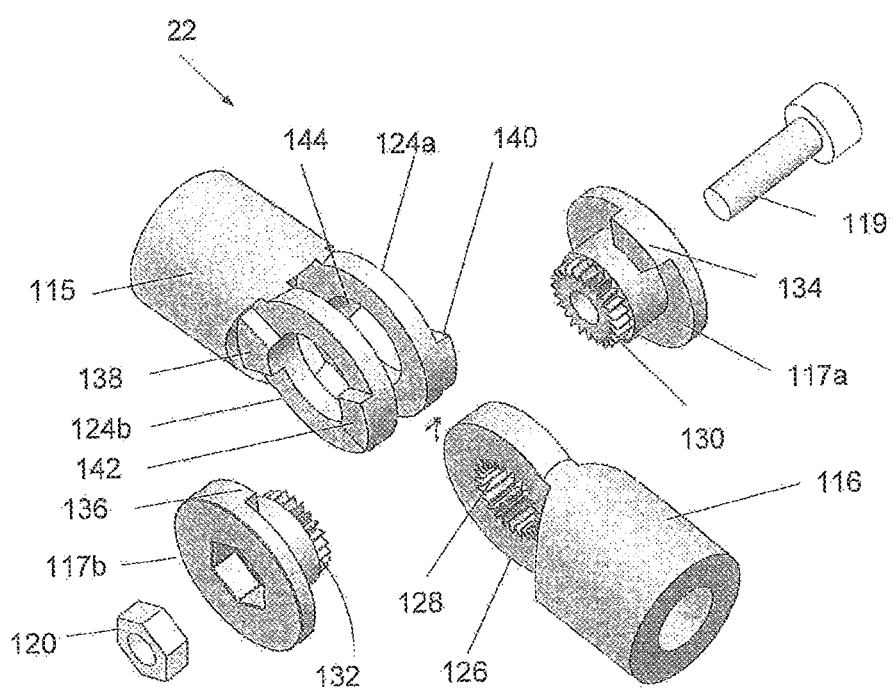

A hinge device 22 is depicted in FIGS. 14 and 15, in assembled and exploded views respectively. The hinge device 22 has a first part 115 hinged to a second part 116, by means of a third part comprising two components 117a, 117b and a nut-and-bolt assembly 119, 120. The first part 115 has a cylindrical body 122 with two rings 124a, 124b, which are spaced apart to receive a ring 126 of the second part 116. Ring 116 has smooth upper and lower surfaces, and teeth 128 on an inner circumferential surface. In use, these engage with teeth 130, 132 on outer circumferential surfaces of the two components 117a, 117b of the third part. The two components can meet approximately half way through the ring member 126. Thus, second and third hinge parts 116, 117 rotate in tandem, relative to the first hinge part 115. Numbers and/or other indicia (not shown for clarity) can be inscribed on one or more of the hinge components, for example on the outer circumferential surfaces of the rings and/or the discs of the components of the third part, for visualisation of a selectable range of pivoting movement.

Figure 16A:
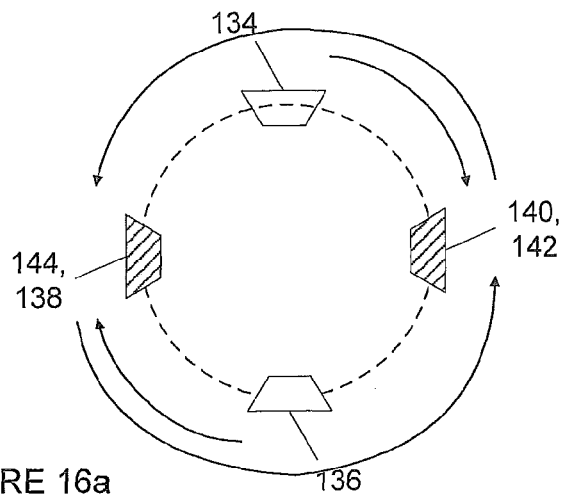
FIGS. 16a to 16c schematically illustrate hinging of the hinging device of FIGS. 14 and 15.
Figure 16B:
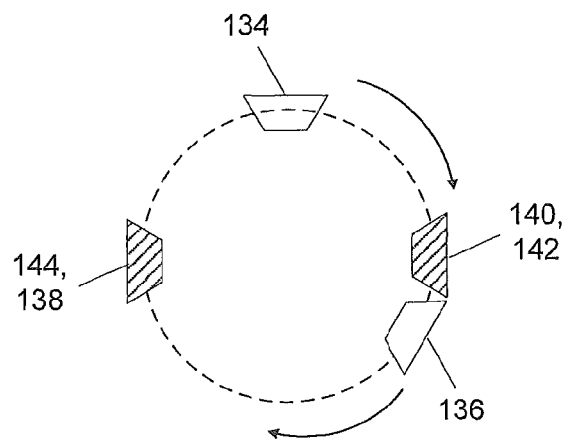
Figure 16C:
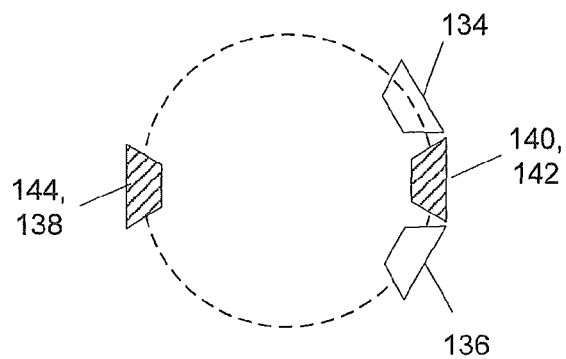

The arc of rotation can be limited by means of the protrusions 134, 136 defined on the two components 117 of the third part, and protrusions 138, 142; 140, 144 on the rings of the first part 115. This can depend on how the relative positions of the protrusions, which is depicted schematically in FIGS. 16a to 16c (viewed from below). The protrusions 138, 142; 140, 144 on the rings 124a, 124b of the first part 115 are shown as overlapping shaded trapezoids, and the protrusions 134, 136 on the two components 117 of the third part are shown as blank trapezoids. In FIG. 16a, protrusions 134, 136 are positioned at opposed points, and can sweep back and forth in an approximately 180-degree arc between protrusions 144, 138 and 140, 142. Meanwhile, in FIG. 16b, protrusion 136 initially abuts the lower protrusion 142, which allows a ninety-degree clockwise rotation until protrusion 134 hits protrusion 140, but hinders anti-clockwise rotation beyond its initial point. In FIG. 16c, all rotation is hindered.

Figure 17:
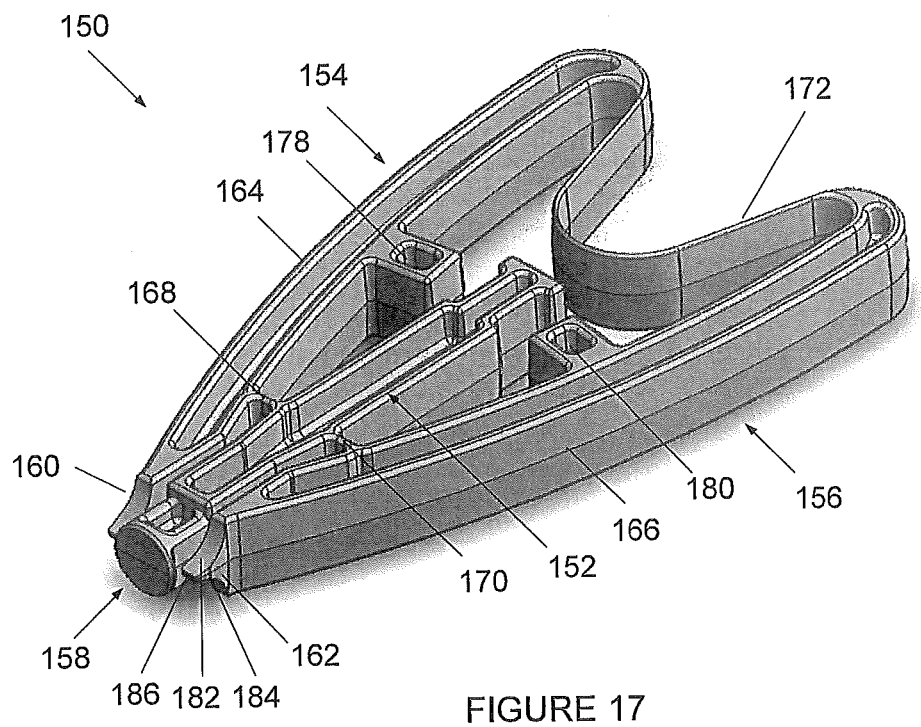
FIGS. 17 and 18 show a perspective and a top view of a disengaging device according to an embodiment of the invention.
Figure 18:
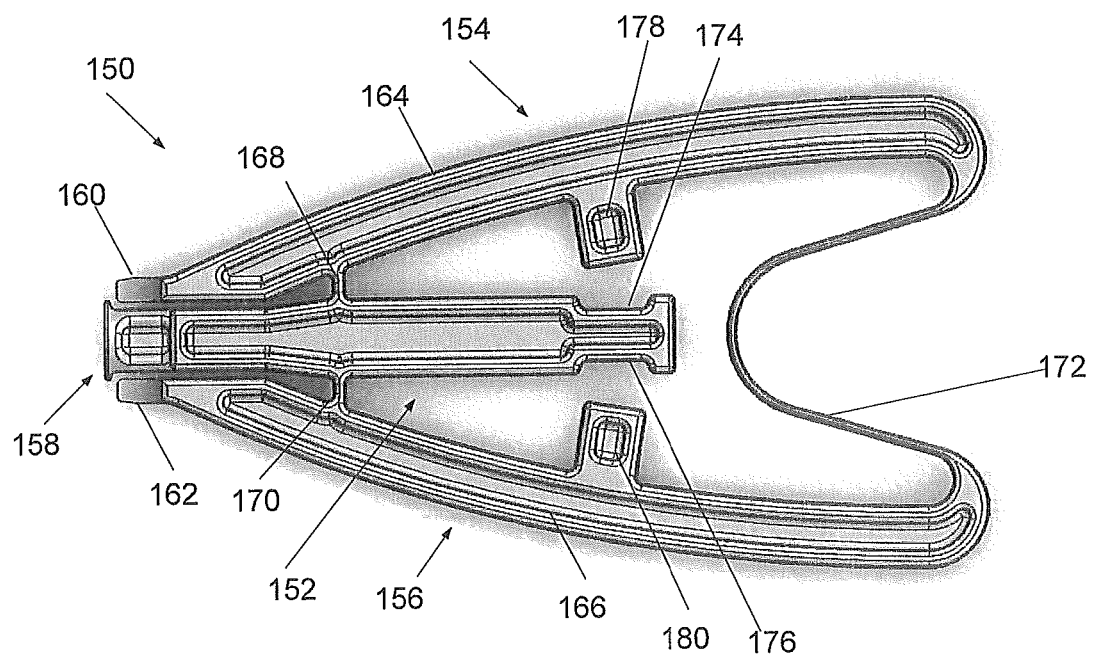

FIGS. 17 and 18 schematically depict a disengaging device 150 for disengaging elements that are linked together in a fixed relationship. The disengaging device 150 is comprised of an elongated body 152 and two handle members 154, 156. The elongated body has a head portion 158 of circular configuration. Disposed on either side of the head portion are jaw portions 160, 162 of the handle members 154, 156. Each of the jaw portions comprises inwardly arcuate surfaces 182, 184 that converge at a lip 186. The grip portions 164, 166 of the handle members extend articulately from the jaw portions across pivot mounts 168, 170 to a connecting spring band 172. The spring band can be a plastic material having "springback" properties. Two indented contact surfaces 174, 176 are formed towards the rear of the elongated body 152, which are aligned with two contact blocks 178, 180 of the handle members.

With reference to FIG. 2, to disengage elements of an articulated bracelet that are in a fixed relationship (e.g. disengaging elements 26c and 26d from elements 24b and 24c), the head portion 158 of the elongated body is positioned in the gap 180 present between elements 24b and 24c. The jaw portions 160, 162 are positioned in the gaps 182, 184 present between the curved shoulders of elements 24b and 24c. Pressing the grip portions towards each other pushes the jaw portions against elements 26c and 26d, loosening them enough to allow final disengagement by hand.

Figure 19:
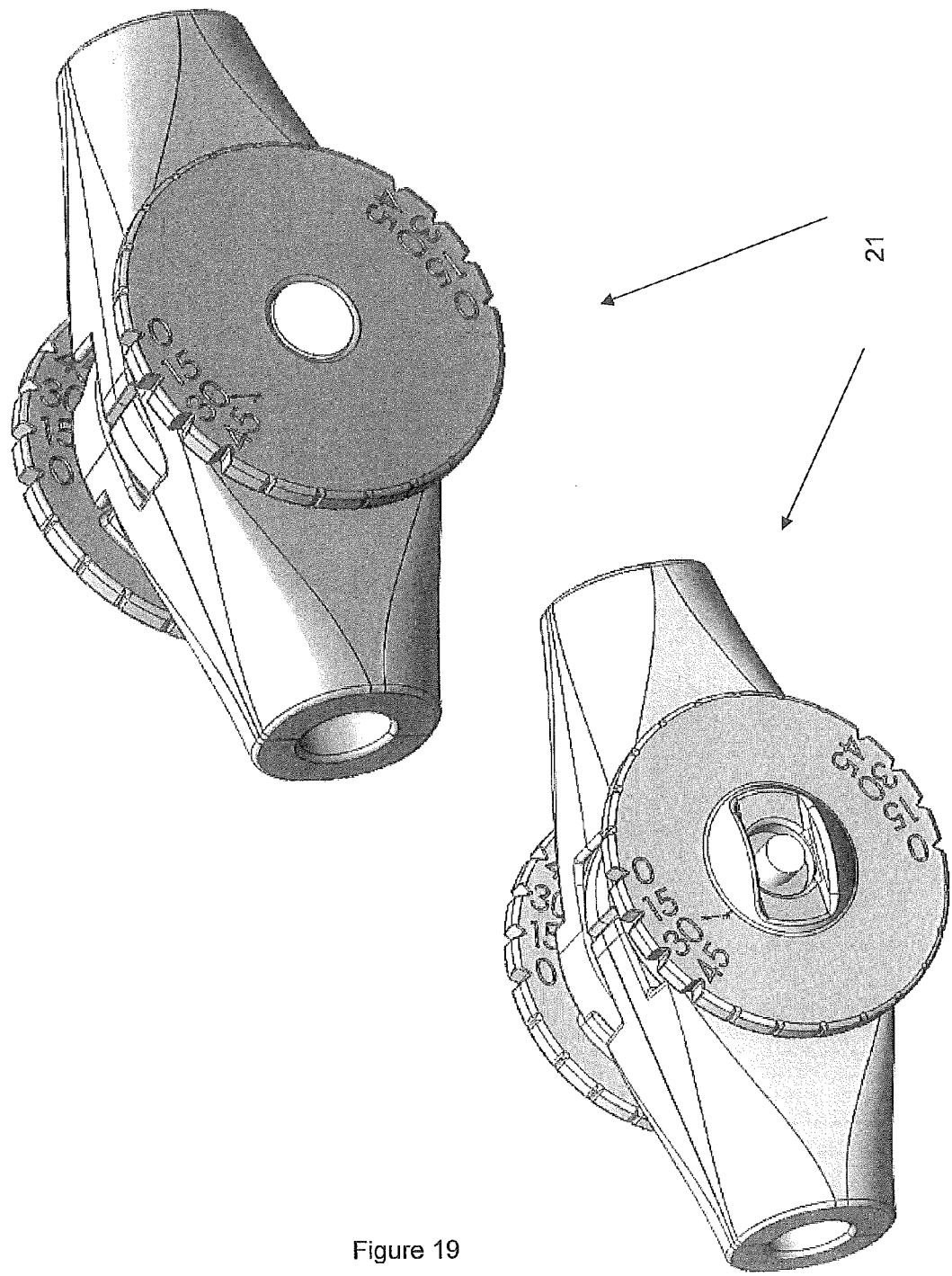
FIG. 19 shows exploded perspective views of the hinge device.

FIG. 19 shows another embodiment of the hinge device. The hinge allows a range of motion because it can be adjusted using the dial (disc) and the numbers inscribed on the dial. The position can be secured by adjusting the central bolt.

Other modifications and variations will be apparent to the skilled person.

The invention claimed is:

1. A non-invasive fixator for fixing a fracture or soft tissue injury comprising
   a first and a second articulated bracelet each bracelet comprising a plurality of elements arranged in a plurality of rows and wherein said bracelet comprises a central row of elements and two outer rows of elements, wherein said elements have complementary linking means to permit linking said rows of elements together in an interchangeably articulated or fixed relationship, wherein one or more of said plurality of elements comprises means for receiving and engaging at least a portion of a connecting device such that the position of the connecting device can be altered around the bracelet or the limb that it is mounted on,
   at least one articulated connecting device on each of said first and second bracelet;
   a rod connecting said at least one articulated connecting device on said first bracelet to said at least one articulated connecting device on said second bracelet, and
   a hinge device.

2. An articulated bracelet for use with an external non-invasive fixator for fixing a fracture or soft tissue injury according to claim 1, the bracelet comprising a plurality of elements arranged in a plurality of rows, wherein said elements have complementary linking means to permit linking said rows of elements together in an interchangeably articulated or fixed relationship, wherein one or more of said plurality of elements comprises means for receiving and engaging at least a portion of a connecting device such that the position of the connecting device can be altered around the bracelet or the limb that it is mounted on.

3. An element for an articulated bracelet according to claim 2 for an external non-invasive fixator for fixing a fracture or soft tissue injury, the element comprising,
   a first kind of element having linking means to permit linking to a second kind of element in an articulated or fixed relationship, said first kind of element comprising a body defining a channel, said channel being partially enclosed by inwardly extending segments and having at least one open end, each of said arcuate projections having one or more laterally extending ridge-like teeth on a first arcuate surface, and one or more arcuate grooves in a second arcuate surface.

4. A disengaging device for disengaging elements of an articulated bracelet as defined in claim 2, having a plurality of elements arranged in a plurality of rows, the rows of elements being linked together in a fixed relationship, the disengaging device comprising:
   an elongated body having a head portion at one end; and
   first and second handle members each having a grip portion and a jaw portion;
   wherein said first and second handle members are pivotally connected to opposite sides of said elongated body, so that when said grip portions move towards each other said jaw portions move away from each other.

5. A method of disengaging elements of an articulated bracelet as defined in claim 1, the disengaging device comprising:
   an elongated body having a head portion at one end; and
   first and second handle members each having a grip portion and a jaw portion;

wherein said first and second handle members are pivotally connected to opposite sides of said elongated body, so that when said grip portions move towards each other said jaw portions move away from each other, the method comprising:
  placing said head portion of said elongated body and said jaw portions of said first and second handle members between two adjacent elements of a first row of said plurality of rows; and
  pressing said grip portions of said first and second handle members towards each other so that said jaw portions push against elements belonging to rows adjacent to said first row.

6. A fixator according to claim 1 wherein one or more elements of said central row comprises said means for receiving and engaging at least a portion of a connecting device such that the position of the connecting device can be altered around the bracelet or the limb that it is mounted on.

7. A fixator according to claim 6 wherein said means for receiving and engaging comprises a channel.

8. A fixator according to claim 1 wherein said linking means comprise:
  at least one arcuate projection extending laterally to said row direction on a first of said elements; and
  at least one arcuate slot for receiving said arcuate projection in a second of said elements;
  wherein said first and second elements belong to adjacent rows, and
  wherein substantially all of the elements of a given said row are of a first kind or a second kind of element.

9. A fixator according to claim 8, wherein a first arcuate surface of said arcuate projection, and/or said slot, is provided with one or more ridge-like teeth.

10. A fixator according to claim 1 wherein said hinge device comprises
  a first hinge part having a pair of spaced first and second ring members;
  a second hinge part having a third ring member pivotably accommodated between said first and second ring members, said third ring member having inwardly directed teeth formed on an inner circumferential surface thereof;
  a third hinge part comprising first and second cylindrical members extending through said first and second ring members respectively, each of said first and second cylindrical members have outwardly directed teeth formed on an outer circumferential surface thereof, for engaging with said inwardly directed teeth of said third ring member; and
  a pin for releasably securing together said first, second and third hinge parts
  wherein said members are made of substantially radiolucent material and said pin is made of substantially radiopaque material and wherein the hinge permits movements in a plurality of planes.

11. A fixator according to claim 10 wherein said first, second and third hinge parts are provided with means for selectively limiting the range of pivoting movement of said second hinge part relative to said first hinge part.

12. A fixator according to claim 1 wherein said plurality of elements comprise first and second kinds of elements, said first kind of elements having a plurality of said arcuate projections and said second kind of elements having a plurality of said slots.

13. A fixator according to claim 1 wherein said central row comprises a plurality of elements of a first kind and said two outer rows each comprise a plurality of elements of a second kind.

14. A fixator according to claim 1 wherein said articulated connecting device comprises a pair of fixable clamp members, movable in a plurality of planes, each member having said channel that can be aligned in opposed relationship with one another to form a hole for receiving a rod, at least one of said pair of clamp members having a part-spherical portion for mating with a complementary part-spherical portion of a support member, said support member being mountable on, or integral with, a spacer portion of a base, wherein said pair of clamp members, said support member and said base are releasably secured together by a pin, and wherein said device is capable of being mounted on a flat surface, rectangular or square and a cylindrical surface.

15. A fixator according to a claim 1 further comprising a cross-linking device, comprising first and second pairs of clamp members, each member having a channel that can be aligned in opposed relationship with the channel of its paired member to form a hole for receiving a rod, said first and second pairs being releasably secured together by a pin.

16. An articulated connecting device for use with an external non-invasive fixator according to claim 1, the connecting device comprising a pair of clamp members, each member having a channel that can be aligned in opposed relationship with one another to form a hole for receiving a rod, at least one of said pair of clamp members having a part-spherical portion for mating with a complementary part-spherical portion of a support member, said support member being mountable on, or integral with, a spacer portion of a base, wherein said pair of clamp members, said support member and said base are releasably secured together by a pin and wherein said device is capable of being mounted on a flat surface, rectangular or square and a cylindrical surface.

17. A cross-linking device for use with a non-invasive fixator according to claim 1, the cross-linking device comprising first and second pairs of clamp members, each member having a channel that can be aligned in opposed relationship with the channel of its paired member to form a hole for receiving a rod, said first and second pairs being releasably secured together by a pin.

18. A hinge device for use with a non-invasive fixator for fixing fractures or soft tissue injuries according to claim 1, the hinge comprising:
  a first hinge part having a pair of spaced first and second ring members;
  a second hinge part having a third ring member pivotably accommodated between said first and second ring members, said third ring member having inwardly directed teeth formed on an inner circumferential surface thereof;
  a third hinge part comprising first and second cylindrical members extending through said first and second ring members respectively, each of said first and second cylindrical members have outwardly directed teeth formed on an outer circumferential surface thereof, for engaging with said inwardly directed teeth of said third ring member; and
  a pin for releasably securing together said first, second and third hinge parts
  wherein said members are made of substantially radiolucent material and said pin is made of substantially radiopaque material and wherein the hinge permits movements in a plurality of planes.

19. A method of treating a fracture, and/or soft tissue injuries, the method comprising securing a non-invasive fixator according to claim 1 to a patient's limb.

* * * * *